(12) United States Patent
Penny

(10) Patent No.: US 11,627,977 B2
(45) Date of Patent: Apr. 18, 2023

(54) WRISTED INSTRUMENT WITH SHARED PITCH AND YAW AXES EXISTING AT THE JAW PIVOT

(71) Applicant: Asensus Surgical US, Inc., Durham, NC (US)

(72) Inventor: Matthew Robert Penny, Holly Springs, NC (US)

(73) Assignee: Asensus Surgical US, Inc., Durham, NC (US)

( * ) Notice: Subject to any disclaimer, the term of this patent is extended or adjusted under 35 U.S.C. 154(b) by 91 days.

(21) Appl. No.: 17/477,502

(22) Filed: Sep. 16, 2021

(65) Prior Publication Data

US 2022/0000511 A1    Jan. 6, 2022

Related U.S. Application Data

(63) Continuation of application No. 16/513,710, filed on Jul. 17, 2019, now Pat. No. 11,134,971.

(51) Int. Cl.
*A61B 17/29* (2006.01)

(52) U.S. Cl.
CPC ...... *A61B 17/29* (2013.01); *A61B 2017/2902* (2013.01); *A61B 2017/2938* (2013.01); *A61B 2017/2939* (2013.01)

(58) Field of Classification Search
CPC .... A61B 2017/2926; A61B 2017/2947; A61B 2017/2931; A61B 2017/2932; A61B 2017/2938; A61B 2017/2939; A61B 2017/294; A61B 2017/2941; A61B 2017/2945; A61B 2017/2902; A61B 2017/0069; A61B 2034/305; A61B 2034/301; A61B 2034/302; A61B 2034/303; A61B 2034/304; A61B 17/29
See application file for complete search history.

(56) References Cited

U.S. PATENT DOCUMENTS 5,752,973 A    5/1998 Kieturakis
2016/0262782 A1*  9/2016 Kalmann ............. A61B 17/282

* cited by examiner

*Primary Examiner* — Majid Jamialahmadi

(57) ABSTRACT

A surgical instrument includes a shaft and a pair of jaw members disposed on the shaft and extending from an at least partially spherical element. The jaw members are moveable in pitch and yaw relative to the center of the sphere in response to actuation forces applied to a proximal drive mechanism of the instrument. The surgical instrument may include a manually operated handle for manual input of actuation forces by a user, or it may be removably mounted to a drive component of a robotic system such that its proximal drive mechanism is operatively engaged with actuators that generate mechanical output that is transferred to the proximal drive mechanism.

9 Claims, 3 Drawing Sheets

WRISTED INSTRUMENT WITH SHARED PITCH AND YAW AXES EXISTING AT THE JAW PIVOT

This application is a continuation of U.S. application Ser. No. 16/513,710, filed Jul. 17, 2019, now U.S. Pat. No. 11,134,971, issued Oct. 5, 2021.

BACKGROUND

In laparoscopic and robotic surgery, wristed and articulating instruments provide additional dexterity for the surgeon—enabling access to tissue in small, constrained spaces. Some such instruments have a single pitch joint and a single yaw joint, while others have multiple joints for pitch and yaw. Still other instruments incorporate a combination of yaw pivot and distal end rotation.

Some of the commercially available instruments using discrete joint instruments (single joint for pitch and yaw), are configured such that the pitch and yaw joints share a single axis. This creates a scenario where the distance from the tip of the instrument end effector to the pitch joint is the same as it is to the yaw joint. Instruments where the pitch and yaw joints do not share the same axis will have different distances from the end effector tip to the respective joints. Having the pitch and yaw joint share the same axis offers the advantages that the overall achievable angle is lower than if the axes were separate.

This application describes end effector embodiments that use a shared axis for pitch and yaw joints, but that also position that axis at the jaw pivot. This will enable use of wristed instruments in extremely small workspaces.

DETAILED DESCRIPTION

This application shows and describes end effectors for a surgical instrument. These end effectors are positioned at the distal end of an instrument shaft. The surgical instrument may be configured for manual operation using a proximal drive mechanism in the form of a manually actuated instrument handle at the proximal end of the instrument shaft. Alternatively, for robotically assisted operation, the instrument's proximal drive mechanism receives motion from robotically controlled actuators operating in accordance with surgeon input to a surgical robotic system. In this latter type of configuration, the instrument may be removably mounted to a drive component of the robotic system such that its proximal drive mechanism is operatively engaged with actuators (e.g. electromechanical actuators, or hydraulic/pneumatic actuators) that generate mechanical output that is transferred to the proximal drive mechanism. The drive component may be an arm that supports the instrument and includes the actuators, or it might be some other form of drive component (e.g. a motor pack) that is engaged with the instrument.

Figure 1:
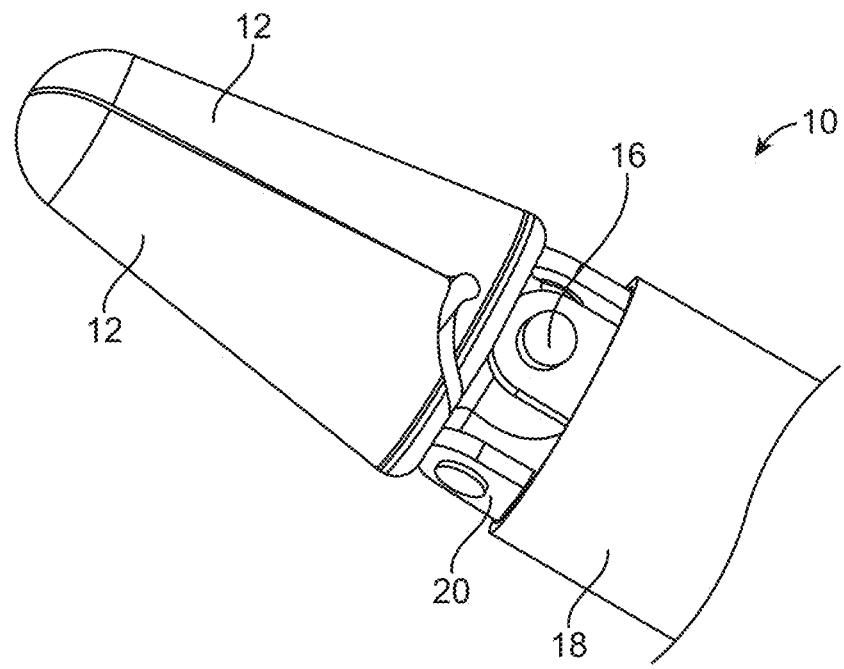
FIG. 1 is a perspective view of an instrument end effector, which uses external pivots.
Figure 2:
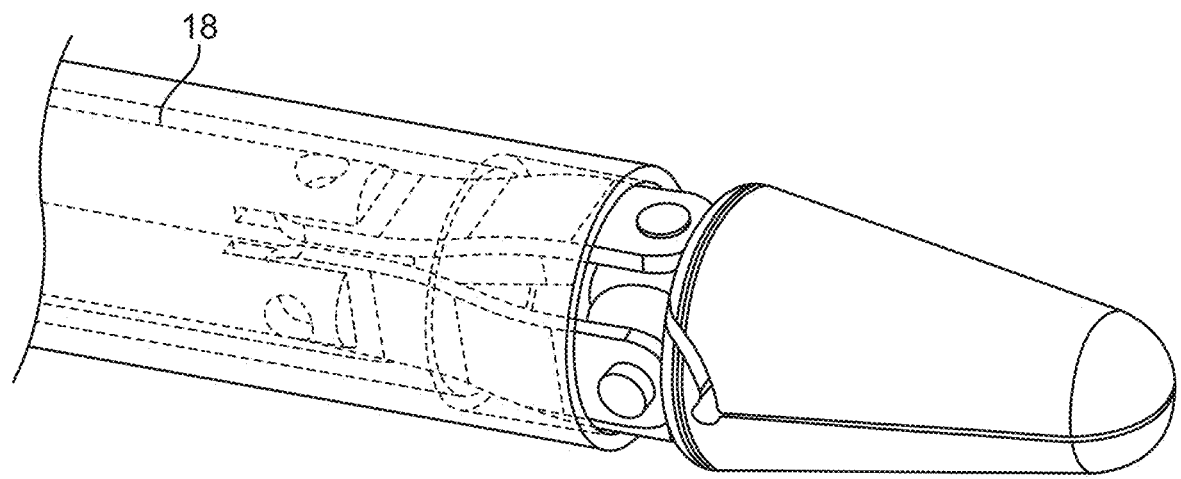
FIG. 2 shows the instrument of FIG. 1 with the shaft made transparent to allow the flatwires to be seen.
Figure 3A:
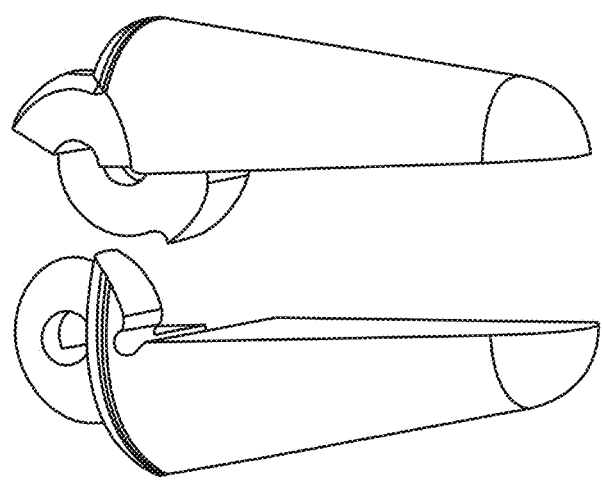
FIGS. 3A-3D are a perspective view, a plan view, a distal end view and a proximal end view, respectively, of the jaw members. In these drawings, the jaw members are separated to allow their features to be more visible.
Figure 3B:
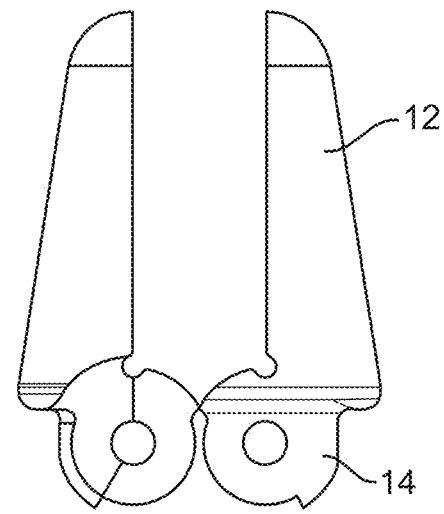
Figure 3C:
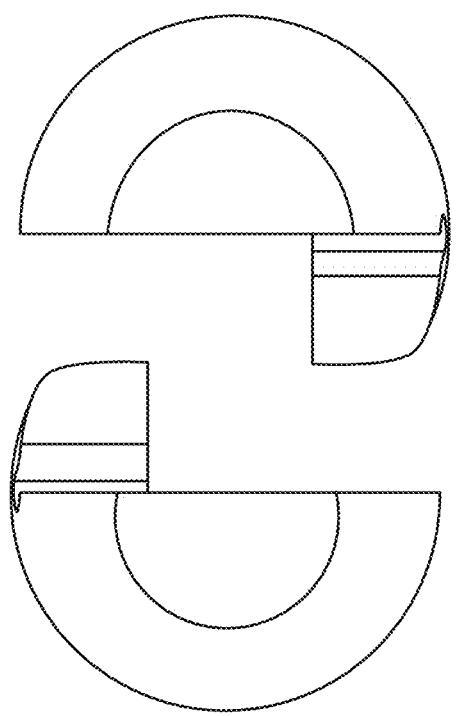
Figure 3D:
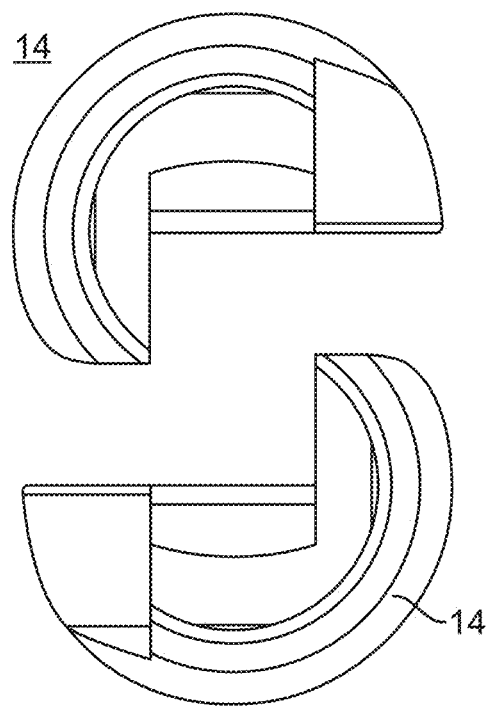

FIG. 1 shows a first embodiment of an instrument 10 having a pair of jaws 12. Each jaw has a base 14 shaped in the form of a portion of a sphere or one half of a sphere. Each base 14 has two pivot pins 16, positioned orthogonal to one another. When the jaws are assembled together, the bases 14 form a sphere (except for the portion from which the jaw members extend) and there are four pins 16 positioned on the same plane, each pin orthogonal to the next.

The shaft 18 of the instrument includes an outer sleeve and four tendons 20 extending from the proximal drive mechanism to the instrument end effector. At the distal end of each tendon, there is a flat wire that extends from the distal side of each tendon to one of the pins 16 on the end effector sphere. The flat wire can pivot both at the pin on the sphere and at the end of the tendon. Alternate embodiments could use a bendable connection between the tendon and the pin.

The flat wire transforms movement of the tendon into movement at the respective pin. The end effector can be articulated in pitch by pushing or pulling on one pair of tendons in opposite directions and articulated in yaw by pushing or pulling on the other pair of tendons in opposite directions. The pitch tendons can also be pushed or pulled in the same direction to open or close the jaw end effector. Additionally, pushing all tendons or pulling all tendons at the same time would extend or retract the end effector from the outer sheath 18 and if the tendons themselves can be rotated relative to the instrument shaft, the end effector may be axially rotated.

Figure 4:
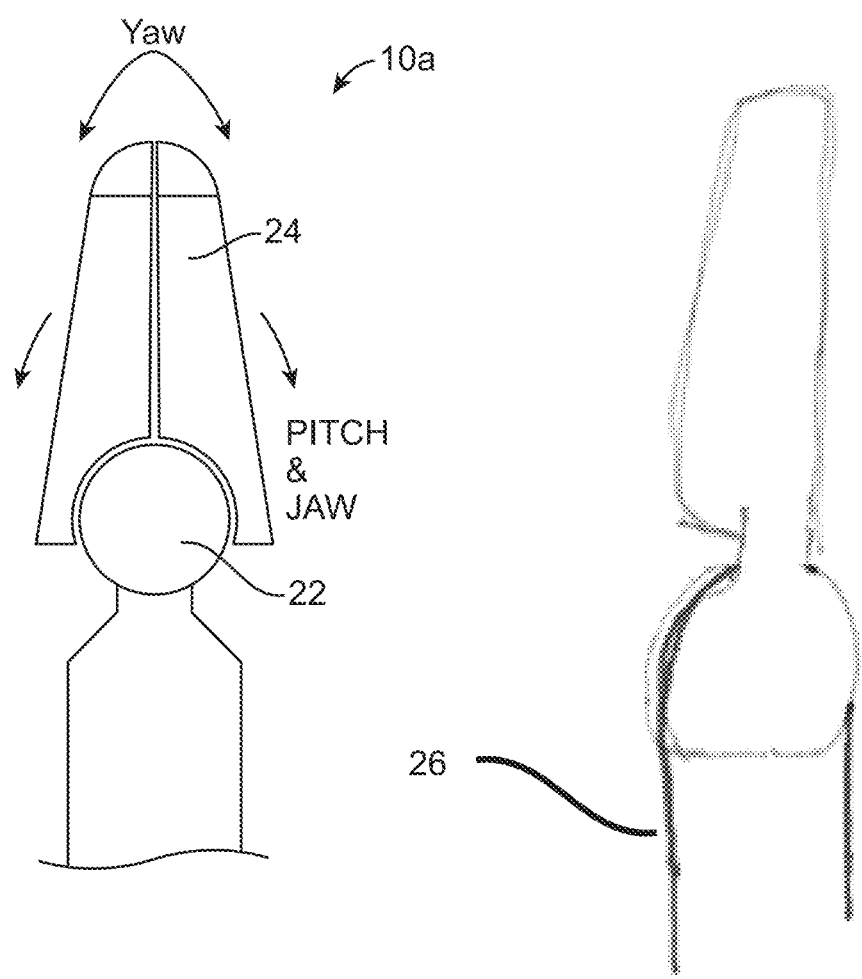
FIG. 4 shows a second embodiment of an instrument end effector, which uses internal pivot points.

A second embodiment 10a of an end effector, shown in FIG. 4, uses an internal ball pivot 22 upon which the jaws of the end effector will rotate. The internal ball 22 is fixed such that each jaw 24 can slide around the ball's outer diameter. The jaws are designed such that assembling them to each other with the ball pivot in between will capture the ball pivot.

The motion of the end effector 10a can be controlled with a similar mechanism to what is described with respect to the first embodiment. Alternatively, as shown in the drawing, the end effector can have two cables 26, each wrapped around a separate jaw such that the center of each cable is fixed to each jaw. The ends of each cable are terminated into adjacent tendons that extend from the distal end of the instrument shaft to the proximal drive mechanism. Pulling on one side of each cable attached to a jaw will move that jaw in pitch, while pulling on both cables for a given jaw will move that jaw in a yaw direction.

What is claimed is:

1. A surgical instrument comprising:
   a shaft;
   a spherical ball member at a distal end of the shaft, said ball member having a geometric center;
   a first jaw member and a second jaw member, each of the first and second jaw members slidably positioned on a surface of the ball member; and
   a first pair of actuation tendons coupled to the first jaw member;
   a second pair of actuation tendons coupled to the second jaw member;
   wherein increasing tension on only one of the tendons in the first pair of actuation tendons causes movement of the first jaw member in a pitch direction and increasing tension on only one of the tendons in the second pair of actuation tendons causes movement of the second jaw member in the pitch direction, wherein movement of the first and second jaw members in the pitch direction is centered at the geometric center of the ball member; and wherein increasing tension on both of the tendons in the first pair of actuation tendons causes movement of the first jaw member in a yaw direction and increasing tension on both of the tendons in the second pair of actuation tendons causes movement of the second jaw member in the yaw direction, wherein movement of the first and second jaw members in the yaw direction is centered at the geometric center of the ball member.

2. The surgical instrument of claim 1, wherein simultaneously increasing tension on only one of the tendons in the first pair of actuation tendons and only one of the tendons in the second pair of actuation tendons causes simultaneous movement of the first and second jaw members in the pitch direction.

3. The surgical instrument of claim 1, wherein simultaneously increasing tension on both of the tendons in the first pair of actuation tendons and both of the tendons in the second pair of actuation tendons causes movement of the first and second jaw members in the yaw direction.

4. The surgical instrument of claim 1, wherein the first pair of actuation tendons comprises a first tendon member fixed to the first jaw member at a center region of the first tendon member.

5. The surgical instrument of claim 1, wherein the surgical instrument includes a handle manually operable to apply force to the first and second pair of actuation tendons.

6. The surgical instrument of claim 1, wherein the surgical instrument is removably attachable to a drive component of a robotic system for delivery of force to the first and second pair of actuation tendons in response to user input commands to the robotic system.

7. A method of using a surgical instrument, the method comprising:
providing a surgical instrument comprising a shaft,
a spherical ball member at a distal end of the shaft, said ball member having a geometric center;
a first jaw member and a second jaw member, each of the first and second jaw members slidably positioned on a surface of the ball member;
a first pair of actuation tendons coupled to the first jaw member; and
a second pair of actuation tendons coupled to the second jaw member;
increasing tension on only one of the tendons in the first pair to cause movement of the first jaw member in a pitch direction;
increasing tension on only one of the tendons in the second pair of actuation tendons to cause movement of the second jaw member in the pitch direction, wherein movement of the first and second jaw members in the pitch direction is centered at the geometric center of the ball member;
increasing tension on both of the tendons in the first pair of actuation tendons to cause movement of the first jaw member in a yaw direction; and
increasing tension on both of the tendons in the second pair of actuation tendons to cause movement of the second jaw member in the yaw direction, wherein movement of the first and second jaw members in the yaw direction is centered at the geometric center of the ball member.

8. The method of claim 7, wherein the surgical instrument is provided to include a handle, and wherein the method includes manually operating the handle to selectively apply force to tension the first and second pair of actuation tendons.

9. The method of claim 7, wherein the method further includes removably attaching the surgical instrument to a drive component of a robotic system, and causing the drive component to deliver force to the first and second pair of actuation tendons in response to user input commands to the robotic system.

* * * * *